United States Patent
Locke et al.

(10) Patent No.: US 10,124,095 B2
(45) Date of Patent: Nov. 13, 2018

(54) INSTILLATION CARTRIDGE FOR VACUUM ACTUATED FLUID DELIVERY

(71) Applicant: KCI Licensing, Inc., San Antonio, TX (US)

(72) Inventors: Christopher Brian Locke, Bournemouth (GB); James A. Luckemeyer, San Antonio, TX (US); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 445 days.

(21) Appl. No.: 14/794,302

(22) Filed: Jul. 8, 2015

(65) Prior Publication Data
US 2016/0015871 A1    Jan. 21, 2016

Related U.S. Application Data

(60) Provisional application No. 62/026,513, filed on Jul. 18, 2014.

(51) Int. Cl.
*A61M 1/00* (2006.01)
*A61M 3/02* (2006.01)
(Continued)

(52) U.S. Cl.
CPC ........ *A61M 1/0031* (2013.01); *A61M 1/0058* (2013.01); *A61M 1/0084* (2013.01);
(Continued)

(58) Field of Classification Search
CPC ..... A61B 17/32; A61B 17/3205; A61B 42/00; A61B 46/00; A61F 13/00017; A61M 1/0031; A61M 1/0058
See application file for complete search history.

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for corresponding PCT Application No. PCT/US2015/039618 dated Oct. 2, 2015.
(Continued)

*Primary Examiner* — Tatyana Zalukaeva
*Assistant Examiner* — Gabriella Burnette

(57) ABSTRACT

A fluid delivery system, method, and apparatus for providing instillation therapy with a negative-pressure source is described. The apparatus includes a housing having an ambient chamber and a negative-pressure chamber fluidly isolated from each other. The apparatus also includes a moveable barrier disposed in the housing between the ambient chamber and the negative-pressure chamber. The moveable barrier is operable to move between a charge position and a discharge position in response to negative pressure. A fluid source is disposed in the negative-pressure chamber and is collapsible in response to movement of the moveable barrier to the discharge position. The apparatus also includes a fluid outlet in fluid communication with the fluid source, a negative-pressure port in fluid communication with the negative-pressure chamber and configured to be coupled to a negative-pressure source, and a vent formed in the housing and fluidly coupled to the ambient chamber.

26 Claims, 4 Drawing Sheets

(51) Int. Cl.
*A61M 35/00* (2006.01)
*A61M 37/00* (2006.01)
*A61F 13/00* (2006.01)

(52) U.S. Cl.
CPC ........ *A61M 1/0088* (2013.01); *A61M 3/0254* (2013.01); *A61M 35/00* (2013.01); *A61M 37/00* (2013.01); *A61F 13/00068* (2013.01); *A61M 1/0035* (2014.02); *A61M 2205/123* (2013.01); *A61M 2205/128* (2013.01); *A61M 2205/3334* (2013.01); *A61M 2205/3337* (2013.01); *A61M 2205/3382* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,180,067 A | 12/1979 | Derlien | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,883 A * | 11/1993 | Hood | A61M 1/0039 604/153 |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,542,918 A * | 8/1996 | Atkinson | A61M 1/0064 417/401 |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 0442857 A1 * | 8/1991 | ............... A47K 5/12 |
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2012162287 A1 | 11/2012 | |

(56) References Cited

FOREIGN PATENT DOCUMENTS

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

INSTILLATION CARTRIDGE FOR VACUUM ACTUATED FLUID DELIVERY

The present invention claims the benefit, under 35 USC § 119(e), of the filing of U.S. Provisional Patent Application Ser. No. 62/026,513, entitled "Instillation Cartridge for Vacuum Actuated Fluid Delivery," by Locke et al., filed Jul. 18, 2014, which is incorporated herein by reference for all purposes.

TECHNICAL FIELD

The invention set forth in the appended claims relates generally to tissue treatment systems and more particularly, but without limitation, to a disposable cartridge for applying instillation therapy with a negative-pressure source.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

In addition, the delivery of therapeutic fluids (e.g. saline or antibiotic fluids) to the tissue site can also provide benefits to healing of a tissue site. Treatment of tissue sites with the delivery of therapeutic fluids may also be referred to as "instillation therapy." Instillation therapy may assist in cleaning the tissue site by aiding in the removal of infectious agents or necrotic tissue. The therapeutic fluids used in instillation therapy may also provide medicinal fluids, such as antibiotics, anti-fungals, antiseptics, analgesics, or other similar substances, to aid in the treatment of a tissue site.

While the clinical benefits of negative-pressure therapy and instillation therapy are widely known, the cost and complexity of negative-pressure therapy and instillation therapy can be a limiting factor in its application, and the development and operation of delivery systems, components, and processes continues to present significant challenges to manufacturers, healthcare providers, and patients.

BRIEF SUMMARY

New and useful systems, apparatuses, and methods for instilling fluids are set forth in the appended claims. Illustrative embodiments are also provided to enable a person skilled in the art to make and use the claimed subject matter. For example, a fluid delivery apparatus for providing instillation therapy with a negative-pressure source is described. The apparatus may include a housing having an ambient chamber and a negative-pressure chamber fluidly isolated from each other. The apparatus may also include a moveable barrier disposed in the housing between the ambient chamber and the negative-pressure chamber. The moveable barrier may be operable to move between a charge position and a discharge position in response to negative pressure. A fluid source may be disposed in the negative-pressure chamber and is collapsible in response to movement of the moveable barrier to the discharge position. The apparatus may also include a fluid outlet in fluid communication with the fluid source, a negative-pressure port in fluid communication with the negative-pressure chamber and configured to be coupled to a negative-pressure source, and a vent formed in the housing and fluidly coupled to the ambient chamber.

Alternatively, other example embodiments may describe a system for providing instillation therapy. The system may include a negative-pressure source and a cartridge coupled to the negative-pressure source. The cartridge may include a housing having an ambient chamber and a negative-pressure chamber fluidly isolated from each other. The cartridge may also include a moveable barrier disposed in the housing between the ambient chamber and the negative-pressure chamber. The moveable barrier may be operable to move between a charge position and a discharge position in response to negative pressure. A fluid source may be disposed in the negative-pressure chamber. The fluid source may be collapsible in response to movement of the moveable barrier to the discharge position. A fluid outlet may be in fluid communication with the fluid source. A negative-pressure port may be in fluid communication with the negative-pressure chamber and configured to be coupled to the negative-pressure source; and a vent may be formed in the housing and fluidly coupled to the ambient chamber.

A method for providing instillation therapy with a negative-pressure source is also described. A negative-pressure source and a cartridge may be provided. The cartridge may include a housing having an ambient chamber and a negative-pressure chamber fluidly isolated from each other, and a barrier disposed in the housing between the ambient chamber and the negative-pressure chamber. The barrier may be operable to move between a charge position and a discharge position in response to negative pressure. The cartridge may also include a fluid source disposed in the negative-pressure chamber. The fluid source may be collapsible. A fluid outlet may be in fluid communication with the fluid source; a negative-pressure port may be in fluid communication with the negative-pressure chamber and configured to be coupled to the negative-pressure source; and a vent may be formed in the housing and fluidly coupled to the ambient chamber. The negative-pressure source may be fluidly coupled to the negative-pressure port, and negative-pressure may be supplied to the negative-pressure chamber move the barrier against the fluid source.

In still another embodiment, an apparatus for providing negative-pressure therapy and instillation therapy is described. The apparatus may include a negative-pressure source and a cartridge having an ambient chamber, a negative-pressure chamber, and a fluid source disposed in the negative-pressure chamber. The apparatus may also include a controller configured to: determine a level of negative pressure provided by the negative-pressure source, calculate an amount of fluid instilled in response to the level of negative pressure, maintain the level of negative pressure if the amount of fluid instilled is less than a therapeutic dose, and stop supplying negative pressure with the negative-pressure source if, the amount of fluid instilled is equal to or greater than a therapeutic dose.

Objectives, advantages, and a preferred mode of making and using the claimed subject matter may be understood best

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
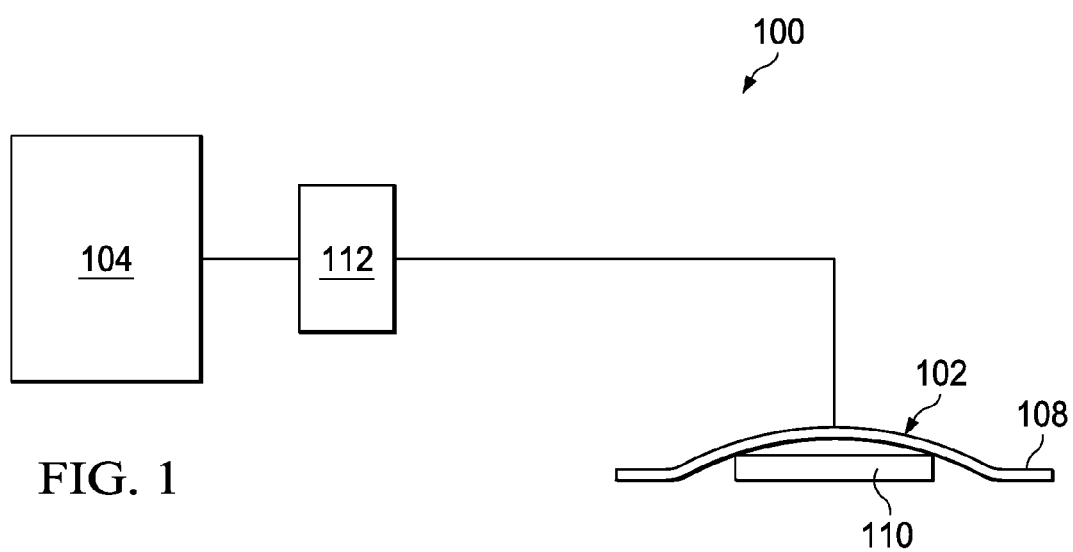
FIG. 1 is a functional block diagram of an example embodiment of a therapy system that can provide instillation fluid in accordance with this specification.

FIG. 1 is a simplified functional block diagram of an example embodiment of a therapy system 100 that can provide instillation therapy in accordance with this specification. The therapy system 100 may include a dressing and a negative-pressure source. For example, a dressing 102 may be fluidly coupled to a negative-pressure source 104, as illustrated in FIG. 1. A dressing generally includes a cover and a tissue interface. The dressing 102, for example, includes a cover 108 and a tissue interface 110. The therapy system 100 may also include a fluid management device, such as a cartridge 112, fluidly coupled to the dressing 102 and to the negative-pressure source 104.

In general, components of the therapy system 100 may be coupled directly or indirectly. For example, the negative-pressure source 104 may be directly coupled to the cartridge 112 and indirectly coupled to the dressing 102 through the cartridge 112. Components may be fluidly coupled to each other to provide a path for transferring fluids (i.e., liquid and/or gas) between the components.

In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected and disposed of properly. The dressing 102 may also provide a sealed therapeutic environment proximate to a tissue site that may allow fluid to be instilled to the tissue site for instillation therapy.

The fluid mechanics of using a negative-pressure source to reduce pressure in another component or location, such as within the cartridge 112, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically refers to a position in a fluid path relatively closer to a negative-pressure source, and conversely, the term "upstream" refers to a position relatively further away from a negative-pressure source. Similarly, it may be convenient to describe certain features in terms of fluid "inlet" or "outlet" in such a frame of reference. This orientation is generally presumed for purposes of describing various features and components of therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to the cartridge 112. In many cases, the local ambient pressure may also be the atmospheric pressure at which a tissue site is located. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy.

A negative-pressure source may include a user interface. A user interface may be a device configured to allow communication between a controller and an environment external to a negative-pressure source. In some embodiments, an external environment may include an operator or a computer system configured to interface with a negative-pressure source, for example. In some embodiments, a user interface may receive a signal from a controller and present the signal in a manner that may be understood by an external environment. In some embodiments, a user interface may receive signals from an external environment and, in response, send signals to a controller.

In some embodiments, a user interface may be a graphical user interface, a touchscreen, or one or more motion tracking devices. A user interface may also include one or more display screens, such as a liquid crystal display ("LCD"), lighting devices, such as light emitting diodes ("LED") of various colors, and audible indicators, such as a whistle, configured to emit a sound that may be heard by an operator. A user interface may further include one or more devices, such as knobs, buttons, keyboards, remotes, touchscreens, ports that may be configured to receive a discrete or continuous signal from another device, or other similar devices; these devices may be configured to permit the external environment to interact with the user interface. A user interface may permit an external environment to select a therapy to be performed with a negative-pressure source. In some embodiments, a user interface may display information for an external environment such as a duration of therapy, a type of therapy, an amount of negative pressure being supplied, an amount of instillation solution being provided, a fluid level of a container, or a fluid level of a cartridge, for example.

A negative-pressure source may also include one or more pressure sensors. A pressure sensor, may be a piezoresistive strain gauge, a capacitive sensor, an electromagnetic sensor, a piezoelectric sensor, an optical sensor, or a potentiometric sensor, for example. In some embodiments, a pressure sensor can measure a strain caused by an applied pressure. A pressure sensor may be calibrated by relating a known amount of strain to a known pressure applied. The known relationship may be used to determine an unknown applied pressure based on a measured amount of strain. In some embodiments, a pressure sensor may include a receptacle configured to receive an applied pressure.

A negative-pressure source may include one or more controllers communicatively coupled to components of the negative-pressure source, such as a valve, a flow meter, a sensor, a user interface, or a pump, for example, to control operation of the same. As used herein, communicative coupling may refer to a coupling between components that permits the transmission of signals between the components. In some embodiments, the signals may be discrete or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. An analog signal may be a continuous signal that includes a time varying feature that represents another time varying quantity. A digital signal may be a signal composed of a sequence of discrete values.

In some embodiments, communicative coupling between a controller and other devices may be one-way communication. In one-way communication, signals may only be sent in one direction. For example, a sensor may generate a signal that may be communicated to a controller, but the controller may not be capable of sending a signal to the sensor. In some embodiments, communicative coupling between a controller and another device may be two-way communication. In two-way communication, signals may be sent in both directions. For example, a controller and a user interface may be communicatively coupled so that the controller may send and receive signals from the user interface. Similarly, a user interface may send and receive signals from a controller. In some embodiments, signal transmission between a controller and another device may be referred to as the controller operating the device. For example, interaction between a controller and a valve may be referred to as the controller: operating the valve; placing the valve in an open position, a closed position, or a metering position; and opening the valve, closing the valve, or metering the valve.

A controller may be a computing device or system, such as a programmable logic controller, or a data processing system, for example. In some embodiments, a controller may be configured to receive input from one or more devices, such as a user interface, a sensor, or a flow meter, for example. In some embodiments, a controller may receive input, such as an electrical signal, from an alternative source, such as through an electrical port, for example.

In some embodiments, a controller may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, a controller may be a programmable logic controller (PLC). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

A negative-pressure source may also include a power source. A power source may be a device that supplies electric power to an electric load. A power source may include a battery, a direct current (DC) power supply, an alternating current (AC) power supply, a linear regulated power supply, or a switched-mode power supply, for example. A power supply may supply electric power to a controller, a sensor, a flow meter, a valve, a user interface, or a pump, for example.

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under a pressure gradient. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to distribute fluid to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between 25-65 grams per square meter (gsm). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The dressing 102 may also be used to provide a sealed therapeutic environment for instillation therapy. Instillation therapy may include the slow introduction of a solution to a tissue site. The solution may be used to provide moisture to the tissue site, to provide warmth or cold to the tissue site, to provide a drug to the tissue site, soak the tissue site in a fluid, or to provide another substance to the tissue site. Often, different types of instillation therapy may require a different type of instillation fluid to achieve a desired effect. For example, a first type of fluid may provide moisture to the tissue site. A different type of fluid may supply a drug to the tissue site. Many times, the need for different types of fluid to treat the tissue site may make instillation therapy time consuming to administer.

Some patients may experience improved outcomes with a combined treatment that includes using both negative-pressure therapy and instillation therapy. Existing therapy systems that provide instillation or irrigation of a tissue site as well as negative-pressure therapy can be complicated to use and setup. Multiple tubes, clamps, and interfaces may often be needed to properly apply both negative pressure and fluid to the tissue site. For example, to set up a therapy system having both negative-pressure therapy and instillation therapy, components for both systems may be placed proximate to a patient. Unfortunately, the cost of a combined treatment system can be prohibitive in many clinical environments, reducing the likelihood that a patient may receive the benefits of both systems.

In many clinical environments, negative-pressure therapy relies on a dedicated therapy system to provide negative-pressure therapy to a tissue site. The dedicated therapy system may be positioned proximate to a patient receiving negative-pressure therapy and the dedicated therapy system may be fluidly coupled to a tissue site to provide negative-pressure therapy. Similarly, instillation therapy often relies on a dedicated instillation therapy system to provide instillation therapy to a tissue site. The dedicated instillation therapy system may also be positioned proximate to a patient receiving instillation therapy, and the dedicated instillation therapy device may be fluidly coupled to a tissue site to provide instillation therapy. Having both therapy system components and instillation therapy system components proximate to a patient may make the area around the patient cluttered, which can lead to negative outcomes for the patient.

Both dedicated negative-pressure therapy systems and dedicated instillation therapy systems may be expensive. Generally, given the costs associated with negative-pressure therapy and instillation therapy, medical facilities may not be willing to purchase both a dedicated negative-pressure therapy system and a dedicated instillation therapy system. As a result, some clinical facilities may choose to forgo some types of clinical treatment. For example, some clinical facilities may maintain a dedicated negative-pressure therapy system to provide negative-pressure therapy. If a patient requires instillation therapy, a clinician may be required to physically administer instillation therapy, such as with a syringe. Application of instillation therapy in this manner may also require the clinician to remove the dressing, which can cause pain to the patient and potentially increase infection risks. Physical administration of instillation therapy can require a significant investment of clinician time, increase the likelihood of misapplication of therapy, and potentially increase the risk of infection of a tissue site.

Some clinical facilities employ multi-channel dedicated negative-pressure therapy systems. A multi-channel negative-pressure therapy system may be capable of providing negative-pressure therapy to more than one tissue site at a time. A multi-channel negative-pressure therapy system may be large and inhibit placement of other devices near a patient. If instillation therapy is also needed, it may be difficult to place a dedicated instillation therapy system proximate to a patient. Consequently, a clinician may be required to physically administer instillation therapy, which can cause some or all of the complications previously described.

The therapy system 100 described herein can solve these problems and others by managing negative-pressure to deliver instillation fluids. In some embodiments, the therapy system 100 can provide negative-pressure therapy to the tissue site. For example, the therapy system 100 can be fluidly coupled to the dressing 102 to provide negative-pressure therapy to a tissue site. In some embodiments, the therapy system 100 can provide instillation therapy to the tissue site. For example, the cartridge 112 can be fluidly coupled to the dressing 102 and the negative-pressure source 104 to use the therapy system 100 to provide instillation therapy.

Figure 2:
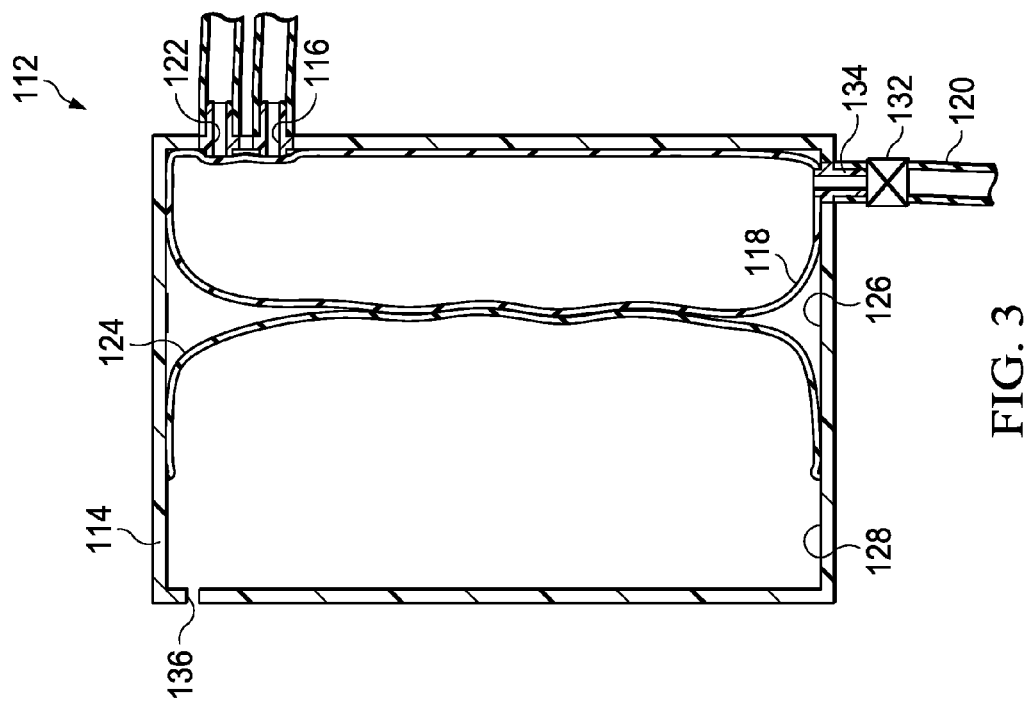
FIG. 2 is a schematic sectional diagram illustrating additional details that may be associated with an example embodiment of a cartridge of the therapy system of FIG. 1.

FIG. 2 is a schematic sectional diagram, illustrating additional details that may be associated with some example embodiments of the cartridge 112. Generally, the cartridge 112 may have many different shapes and sizes. In some embodiments, the cartridge 112 may be manufactured to physically couple to existing negative-pressure therapy products. For example, the cartridge 112 and the components described below may be manufactured to resemble a canister, such as a Bemis canister, that can be coupled to the negative-pressure source 104. In other embodiments, the cartridge 112 may be manufactured to resemble a canister for a V.A.C. ULTA™ negative-pressure wound therapy system manufactured by Kinetic Concepts, Inc. In still other embodiments, the cartridge 112 may be manufactured to resemble a canister for an InfoV.A.C.® negative-pressure therapy system manufactured by Kinetic Concepts, Inc.

The cartridge 112 may have a housing 114. In some embodiments, the housing 114 may form an outer portion of the cartridge 112. In other embodiments, the housing 114 may be disposed inside another container so that the housing 114 may be enclosed in the cartridge 112. In some embodiments, the housing 114 may generally define a chamber and have a structural arrangement to fluidly isolate the chamber from the ambient environment. In some embodiments, the housing 114 may be cubic in shape and form a cubic chamber having a square cross-section. In other embodiments, the housing 114 may have other suitable shapes, such as spherical, ovoid, or amorphous shaped, which may form similarly shaped chambers having similarly shaped cross-sections. In some embodiments, the shape of the chamber may not correspond with the shape of the housing 114. In some embodiments, the housing 114 may be formed of EASTAR™ DN004 produced by Eastman Chemical Company. In other embodiments, the housing 114 may be formed of Terlux® 2802HD or Terlux® 2822HD produced by Styrolution Group GmbH.

In some embodiments, a fluid source 118 may be disposed in the housing 114. The fluid source 118 may be a reservoir of fluid placed in the chamber of the housing 114. In some embodiments, the fluid may be fluidly isolated from the chamber of the housing 114 so that fluid may not flow from the fluid source 118 into the chamber of the housing 114. In some embodiments, the fluid source 118 may be sealed to the housing 114. In some embodiments, the fluid source 118 may be a bag of fluid, such as a 1000 milliliter bag of instillation fluid, placed inside the chamber of the housing 114. In some embodiments, the fluid source 118 may be formed of a flexible plastic, such as polyvinyl chloride. In some embodiments, the fluid source 118 may be collapsible or compressible. The housing 114 may be sized to hold varying volumes of fluid. For example, in some embodiments, the fluid source 118 may hold 1000 milliliters of fluid, and the housing 114 may be sized to hold the 1000 milliliter fluid source. In other embodiments, the fluid source 118 may hold more or less fluid, and the housing 114 may be sized correspondingly. In some embodiments, the housing 114 may include an opening or a hinged wall that permits the fluid source 118 to be removed and replaced. In other embodiments, the fluid source 118 may not be removed from the housing 114.

In some embodiments, a barrier may be disposed within the chamber of the housing 114. A barrier may be a solid object positioned within the chamber of the housing 114 to divide the chamber of the housing 114 into two separate fluid chambers. In some embodiments, a portion or an entirety of a barrier may be movable, such as a piston or a diaphragm 124, to adjust respective volumes of the chambers created by the barrier. In some embodiments, the diaphragm 124 may be a membrane or a sheet of semi-flexible material having a periphery. The periphery of the diaphragm 124 may be coupled to the housing 114 to form a negative-pressure chamber 126 and an ambient chamber 128. Generally, the periphery of the diaphragm 124 may be coupled to the housing 114 so that the negative-pressure chamber 126 is fluidly isolated from the ambient chamber 128. For example, the diaphragm 124 may be sealed to the housing 114, may be welded to the housing 114, may be adhered to the housing 114, or may be otherwise coupled to the housing 114 to prevent fluid movement across the diaphragm 124. In some embodiments, the diaphragm 124 may be formed of an elastic or a semi-elastic material. In some embodiments, the diaphragm 124 may be formed of rubber, thermoplastic, or polytetrafluoroethlyene. In some embodiments, the diaphragm 124 may be formed of a polyurethane film, a polymer of butyl, epichlorohydrin, vinyl acrylic (also known as Vamac®), polychloroprenen, chlorosulphonated polyethylene (Hypalon®), PEBAX®, thermoplastic elastomers (such as Medalist®, Kraton®, or Kraiburg®), and thermoplastic vulcanizates (such as Santoprene®).

In some embodiments, the periphery of the diaphragm 124 may be coupled to the housing 114 so that the diaphragm 124 may flex between a discharge position and a charge position. The discharge position of the diaphragm 124 may be the position of the diaphragm 124 that maximizes the volume of the ambient chamber 128 and minimizes the volume of the negative-pressure chamber 126. The charge position of the diaphragm 124 may be the position of the diaphragm 124 that maximizes the volume of the negative-pressure chamber 126 and minimizes the volume of the ambient chamber 128. In some embodiments, the periphery of the diaphragm 124 may be coupled proximate to a center of a cross-section of the housing 114. For example, the housing 114 may kaki a cube. In some embodiments, the periphery of the diaphragm 124 may be coupled to the housing 114 so that the diaphragm 124 coincides with a line bisecting opposing walls of the housing 114 if the volumes of the negative-pressure chamber 126 and the ambient chamber 128 are equal. In other embodiments, the diaphragm 124 may be coupled to the housing 114 in other locations of the housing 114. For example, as shown in FIG. 2, the housing 114 has at least two pairs of opposing walls. The diaphragm 124 may be coupled to a first pair of opposing walls of the housing 114 and may be parallel to a second pair of opposing walls of the housing 114. In some embodiments, the diaphragm 124 may be coupled to the housing 114 so that the diaphragm 124 is closer to one of the second pair of opposing walls than the other.

In some embodiments, the dimensions of the diaphragm 124, the negative-pressure chamber 126, and the ambient chamber 128 may be determined by a size of the housing 114. In some embodiments, the housing 114 may be sized to hold a 1000 milliliter fluid source 118. The diaphragm 124, the negative-pressure chamber 126, and the ambient chamber 128 may be sized to accommodate the volume of the fluid source 118 while operating as described herein.

In some embodiments, the housing 114 may have a negative-pressure port 122. The negative-pressure port 122 may be a fluid passage formed in the housing 114 to provide fluid communication with the negative-pressure chamber 126. In some embodiments, the negative-pressure port 122 may be a tube having at least one lumen. The tube may be coupled to the housing 114 so that the lumen of the tube is in fluid communication with the negative-pressure chamber 126. In some embodiments, the negative-pressure port 122 may be further fluidly coupled to the negative-pressure source 104. In some embodiments, a filter may be disposed in the negative-pressure port 122. For example, a hydrophobic filter may be disposed in the negative-pressure port 122.

In some embodiments, the cartridge 112 may include a sensing port 116. The sensing port 116 may be a fluid passage coupled to the housing 114. In some embodiments, the sensing port 116 may be a tube having at least one lumen. The tube may be coupled to the housing 114 so that a lumen of the tube is in fluid communication with the negative-pressure chamber 126. In some embodiments, the sensing port 116 may be further fluidly coupled to the negative-pressure source 104.

In some embodiments, the cartridge 112 may also have a fluid outlet 120. The fluid outlet 120 may be a fluid passage coupled to the fluid source 118 to provide a fluid path out of the housing 114. In some embodiments, the fluid outlet 120 may be a tube having at least one lumen. The tube may be coupled to the housing 114 so that a lumen of the tube is in fluid communication with the fluid source 118. In some embodiments, the fluid outlet 120 may be further fluidly coupled to a dressing, such as the dressing 102. If the fluid outlet 120 is fluidly coupled to the dressing 102, the dressing 102 may be in fluid communication with the fluid source 118 through the fluid outlet 120.

In some embodiments, the cartridge 112 may include a calibrated orifice 134. A calibrated orifice may be a nozzle, aperture, opening, porthole, spout, or vent, having a predetermined internal diameter. The calibrated orifice 134 may be fluidly coupled to the fluid outlet 120. In some embodiments, the calibrated orifice 134 may be coupled to the fluid outlet 120 so that fluid flowing from the fluid source 118 flows through the calibrated orifice 134.

In some embodiments, the cartridge 112 may include an occluder 132. In some embodiments, the occluder 132 may be fluidly coupled to the fluid outlet 120. In some embodiments, the occluder 132 may be coupled to the housing 114 and the fluid outlet 120 may be coupled to the occluder 132 so that the occluder 132 is fluidly coupled in the fluid path provided by the fluid outlet 120. In some embodiments, the occluder 132 may be fluidly coupled to the calibrated orifice 134 so that the calibrated orifice 134 is upstream from the occluder 132. In other embodiments, the occluder 132 may be coupled in other locations. In some embodiments, the occluder 132 may have a first port, a second port, and a membrane disposed between the first port and the second port. If positive pressure is supplied to the first port, the first port may be in fluid communication with the second port. If negative-pressure is supplied to the second port, the first port and the second port may not be in fluid communication. Generally, if negative pressure is supplied downstream of the occluder 132, the occluder 132 may prevent fluid communication of the negative-pressure through the occluder 132. An occluder may be described in more detail with respect to U.S. patent application Ser. No. 13/323,223, filed Dec. 12, 2011, which is incorporated by reference herein for all purposes. For example, if the fluid outlet 120 is fluidly coupled to a dressing and negative-pressure is supplied to the dressing, the occluder 132 may prevent fluid communication of the negative pressure to the fluid source 118 through the fluid outlet 120.

In some embodiments, the housing 114 may have a vent 136. The vent 136 may be an opening formed in the housing 114, In some embodiments, the vent 136 may be in fluid communication with the ambient chamber 128. In some embodiments, the vent 136 may fluidly couple the ambient chamber 128 to the ambient environment so that the ambient chamber 128 may be maintained at ambient pressure.

Figure 3:
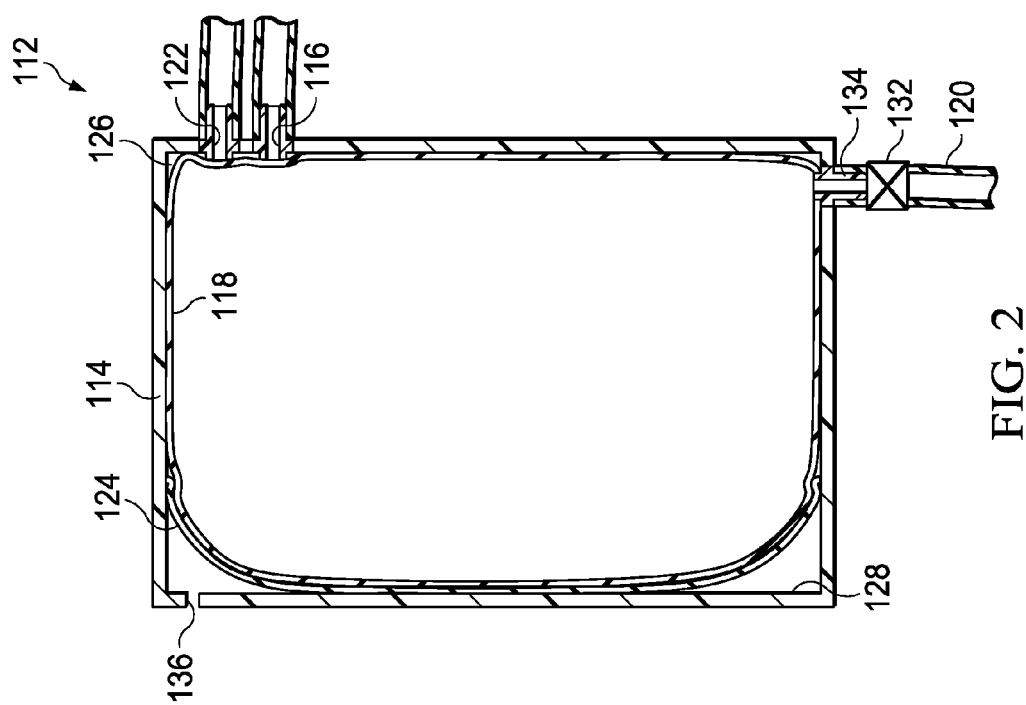
FIG. 3 is a schematic sectional diagram illustrating additional details that may be associated with an operative embodiment of the cartridge of FIG. 2.

FIG. 3 is a schematic sectional diagram illustrating additional details that may be associated with some example embodiments of the cartridge 112. As shown in FIG. 3, the diaphragm 124 may be in the discharge position. In operation, the negative-pressure source 104 may generate a negative-pressure in the negative-pressure chamber 126 by drawing fluid from the negative-pressure chamber 126 through the negative-pressure port 122. As a negative pressure is generated in the negative-pressure chamber 126, the pressure differential between the negative pressure in the negative-pressure chamber 126 and the ambient pressure in the ambient chamber 128 may generate a force that acts on the diaphragm 124. The force caused by the differential pressure may cause the diaphragm 124 to move toward the negative-pressure port 122. In response, the movement of the diaphragm 124 toward the negative-pressure port 122 compresses the fluid source 118, forcing fluid from the fluid source 118, through the calibrated orifice 134, through the occluder 132, and to the dressing 102.

In some embodiments, negative pressure may be generated in the negative-pressure chamber 126 by the negative-pressure source 104. The negative pressure in the negative-pressure chamber 126 may be communicated to a controller of the negative-pressure source 104 through the sensing port 116 that may be fluidly coupled to the negative-pressure source 104. In response, the controller of the negative-pressure source 104 may determine a level of negative pressure in the negative-pressure chamber 126. In some embodiments, the inner diameter of the calibrated orifice 134 may be predetermined and provided to the controller of the negative-pressure source 104. The controller may then determine a rate of fluid flow through the calibrated orifice 134 based on the inner diameter of the calibrated orifice 134 and the level of negative pressure in the negative-pressure chamber 126. The controller of the negative-pressure source 104 may then maintain a level of negative pressure in the negative-pressure chamber 126 for a period of time until a therapeutic dose of instillation fluid has been supplied through the fluid outlet 120. A therapeutic dose of instillation fluid may be a volume of fluid required to be delivered to a tissue site to provide suitable therapeutic benefits to the tissue site. In some embodiments, the therapeutic dose may be an entire volume of the fluid source 118. In other embodiments, a therapeutic dose may be less than an entire volume of the fluid source 118. If a therapeutic dose of fluid has passed through the fluid outlet 120, the controller may stop drawing fluid from the negative-pressure chamber 126 and allow the negative-pressure chamber 126 to vent to the ambient pressure, stopping flow through the fluid outlet 120.

In other embodiments, the chamber of the housing 114 may include a diaphragm 124 coupled to each wall of the housing 114. For example, the negative-pressure chamber 126 may have a diaphragm 124 on each side of the negative-pressure chamber 126. In some embodiments, the ambient chamber 128 may be multiple chambers, each having a separate vent 136 coupling the ambient chamber 128 to the ambient environment. In other embodiments, the negative-pressure chamber 126 may be a flexible bag having the fluid source 118 disposed therein. Operation of the negative-pressure source 104 may generate a negative pressure in the negative-pressure chamber 126, and the diaphragms 124 may compress the fluid source 118 as described.

Figure 4:
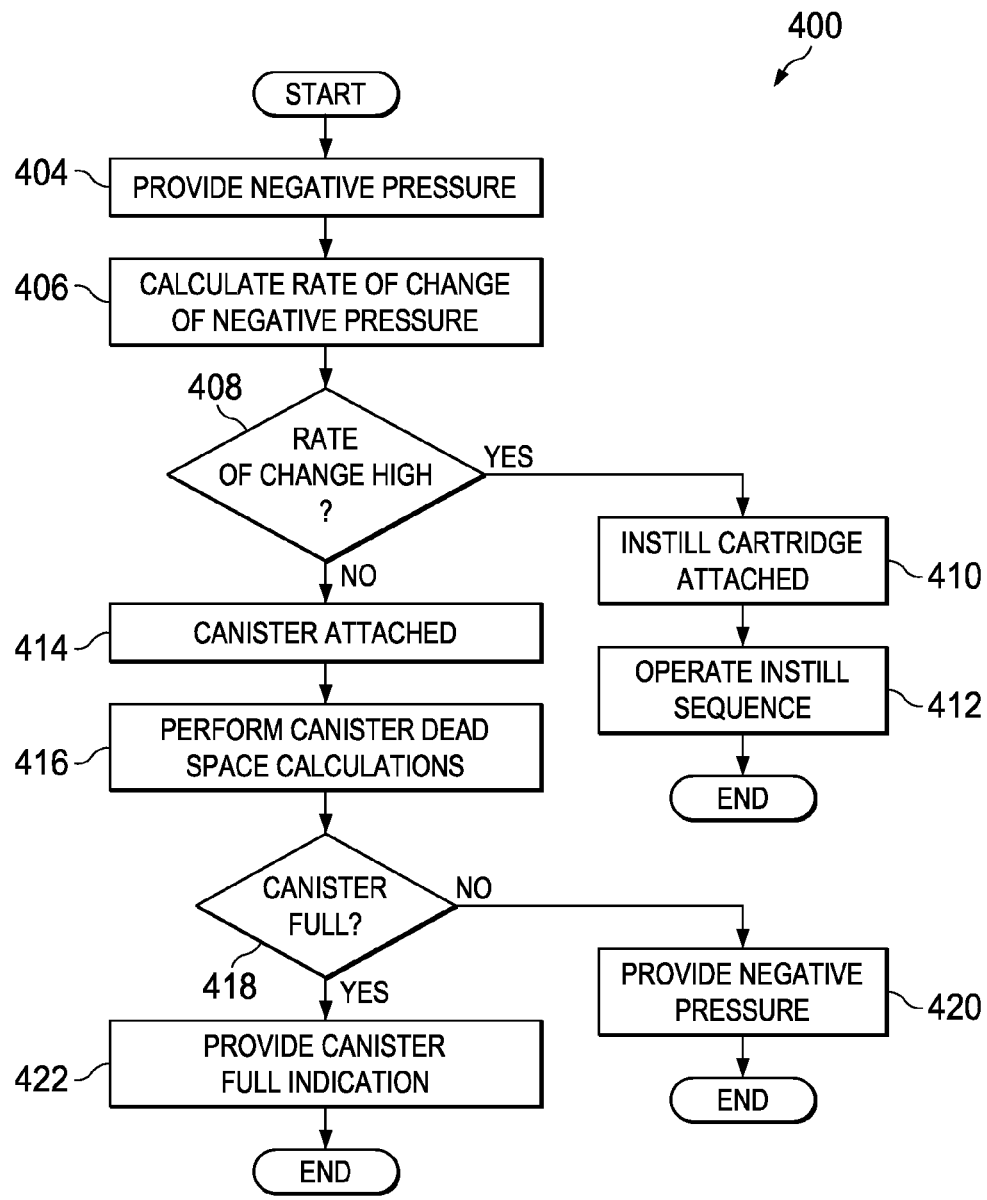
FIG. 4 is a flow chart depicting logical operational steps of a method for providing instillation therapy in accordance with some embodiments.

FIG. 4 is a flow chart 400 illustrating exemplary logical operations that can be implemented in some embodiments of the therapy system 100. For example, the operations may be implemented by a controller operably associated with a negative-pressure source, such as the negative-pressure source 104, configured to execute the operations. In some embodiments, the negative-pressure source 104 may have a mechanical apparatus adapted to be operated by a clinician for the selection of instillation or negative-pressure therapy. For example, the negative-pressure source 104 may include a switch, sensor, or other user interface that allows a user to select between instillation therapy and negative-pressure therapy. In some embodiments, the negative-pressure source 104 may include software or other control devices to distinguish between a fluid instillation cartridge, such as the cartridge 112, and other types of fluid management devices coupled to the negative-pressure source 104. For example, a collection canister may be distinguished from an instillation cartridge. In these embodiments, the negative-pressure source 104 may then provide negative-pressure therapy or instillation therapy based on the determination of the type of fluid management devices fluidly coupled to the negative-pressure source 104.

At block 404, a negative-pressure source may be operated to provide negative pressure to the cartridge. For example, a controller of the negative-pressure source 104 may operate the negative-pressure source 104. At block 406, a rate of change of negative-pressure may be calculated. For example, a controller of the negative-pressure source 104 may calculate the rate of change of negative pressure based on one or more pressure readings from a pressure sensor located in the negative-pressure source 104. In some embodiments, the rate of change of negative pressure may indicate how quickly or slowly the negative pressure in the negative-pressure chamber 126 is increasing within a time period. In some embodiments, the time period may be predetermined. For example, the time period may correspond to a known amount of time that may be required to evacuate a collection canister. At block 408, it can be determined if the rate of change of the negative pressure is greater than a threshold rate of change of the negative pressure. In some embodiments, if a collection canister for negative-pressure therapy is fluidly coupled to the negative-pressure source 104, the rate of change of negative pressure may be within a predetermined range. Similarly, if the cartridge 112 is fluidly coupled to the negative-pressure source 104, the rate of change of negative pressure may fall within a different predetermined range. For example, a collection canister for negative-pressure therapy may have a larger volume than the negative-pressure chamber 126 of the cartridge 112. Because the canister has a larger volume, the threshold rate of change of negative pressure may be lower than the threshold rate of change of negative pressure for the cartridge 112. For example, a controller of the negative-pressure source 104 may determine if the rate of change of negative pressure is within the predetermined rate of change for the cartridge 112, that is, high. In other embodiments, a controller of the negative-pressure source 104 may be programmed to compare the rate of change of negative pressure to a threshold rate of change of negative pressure for the cartridge 112. If a controller is programmed to compare the rate of change of negative-pressure to the threshold rate of change of negative pressure for the cartridge 112, a controller may determine if the rate of change of negative pressure is less than the threshold rate of change of negative pressure, that is, low.

If rate of change of the negative pressure exceeds the threshold, it may be inferred at block 410 that a cartridge for providing instillation therapy is fluidly coupled to the negative-pressure source. For example, a controller of the negative-pressure source 104 may determine that the cartridge 112 is fluidly coupled to the negative-pressure source 104. At block 412, a negative-pressure source may be operated in an instill mode or an instill sequence to provide instillation therapy to a tissue site. For example, a controller of the negative-pressure source 104 may operate the negative-pressure source 104 and the cartridge 112 as described above with respect to FIGS. 2-3 to provide instillation therapy to a tissue site.

At block 408, if the rate of change of negative pressure is less than the threshold, it may be inferred at block 414 that a collection canister or other fluid management device for negative-pressure therapy is fluidly coupled to the negative-pressure source. For example, a controller of the negative-pressure source 104 may determine that a canister for negative-pressure therapy is fluidly coupled to the negative-pressure source 104. At block 416, dead space can be calculated. For example, a controller of the negative-pressure source 104 may perform dead space calculations for the canister. In some embodiments, the amount of dead space in a canister may be calculated by supplying a negative-pressure to the canister and monitoring the rate of change to determine the empty volume of the canister. At block 418, the calculations of the dead space can be used to determine if a fluidly coupled canister is full. For example, a controller of the negative-pressure source 104 can determine if a fluidly coupled canister is full.

At block 418, if the canister is not full, a negative-pressure source can provide negative-pressure therapy at block 420. For example, a controller of the negative-pressure source 104 can operate the negative-pressure source 104 to provide negative-pressure therapy to a tissue site. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa). At block 418, if the canister is full, a full canister indication may be provided at block 422. For example, a controller may provide a full canister indication on a user interface of the negative-pressure source 104.

Figure 5:
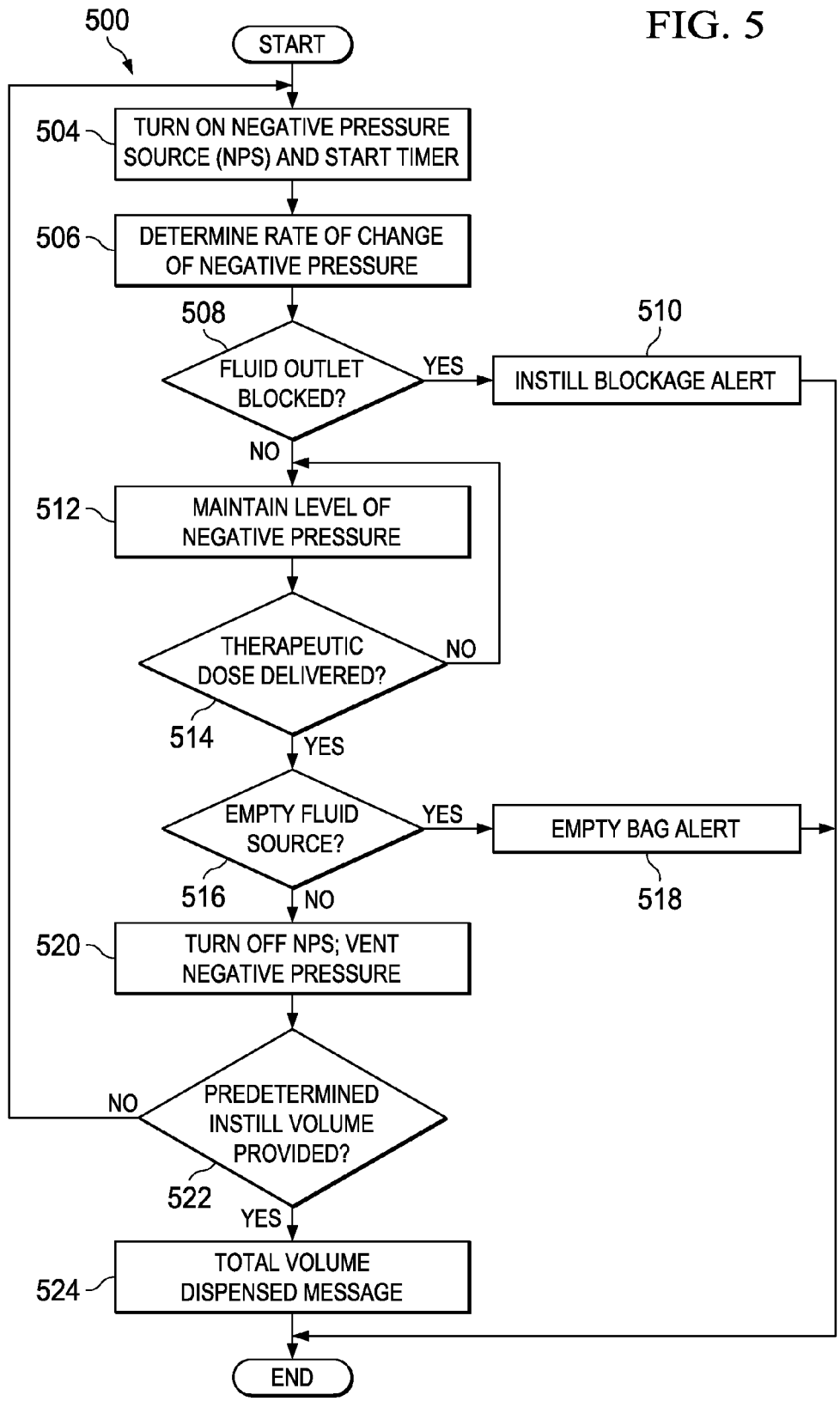
FIG. 5 is a flow chart depicting logical operational steps of another method for providing instillation therapy in accordance with some embodiments.

FIG. 5 is a flow chart 500 illustrating exemplary logical operations for an instill sequence that can be implemented in some embodiments of the therapy system 100 of FIG. 1. For example, the operations may be implemented by a controller in a negative-pressure source, such as the negative-pressure source 104, configured to execute the operations. At block 504, a negative-pressure source may be turned on and a timer started. For example, a controller of the negative-pressure source 104 may turn on a pump in the negative-pressure source 104 to generate a negative pressure at a predetermined pressure setting in the cartridge 112 and may start a timer in the negative-pressure source 104.

At block 506, a rate of change of negative pressure can be determined. For example, a controller of the negative-pressure source 104 can determine the rate of change of negative pressure in the negative-pressure chamber 126 through the sensing port 116 during a predetermined period of time. In some embodiments, the predetermined period of time may be an expected time period during which the negative-pressure chamber 126 may be evacuated. In some embodiments, the expected time period may vary based on the size of the fluid source 118, and the level of fluid in the fluid source 118.

At block 508, it can be determined if the fluid outlet is blocked. For example, a controller of the negative-pressure source 104 can determine if the fluid outlet 120 is blocked. For example, if the rate of change of negative pressure previously determined is within a predetermined tolerance of zero, the pressure in the negative-pressure chamber 126 may not be increasing, indicating that no fluid may be flowing through the fluid outlet 120. At block 508, if the fluid outlet is blocked, an instill blockage error may be provided. For example, a controller of the negative-pressure source 104 may provide an instill blockage error on a user interface of the negative-pressure source 104.

At block 508, if the fluid outlet is not blocked, a level of negative pressure may be maintained at block 512. For example, a level of negative pressure, such as −100 mm Hg, may be maintained in the negative-pressure chamber 126. In some embodiments, a controller may monitor the negative pressure in the negative-pressure chamber 126 and operate the negative-pressure source 104 to maintain a level of negative pressure in the negative-pressure chamber 126 within a predetermined range. At block 514, a negative-pressure source can determine if a therapeutic dose has been dispensed. For example, a controller of the negative-pressure source 104 can determine a flow rate through the fluid outlet 120 based on the level of negative pressure in the negative-pressure chamber 126 and the inner diameter of the calibrated orifice 134. The controller can monitor the timer to determine how much fluid has passed through the fluid outlet 120 based on the length of time measured by the timer. At block 514, if a therapeutic dose of fluid has not been delivered, the level of negative pressure may be maintained at block 512.

At block 514, if a therapeutic dose of fluid has been provided, a status of the fluid source may be determined at block 516. For example, a controller of the negative-pressure source 104 may perform dead space calculations on the negative-pressure chamber 126 to determine if the fluid source 118 is empty. In some embodiments, a negative-pressure may be supplied to negative-pressure chamber 126 and the rate of change of negative pressure may be monitored. The rate of change of negative pressure may be related to an empty volume of the negative-pressure chamber 126 to determine the volume of empty space in the negative-pressure chamber 126. The remaining volume of the fluid in the fluid source 118 may be inferred from the volume of empty space in the negative-pressure chamber 126. At block 516, if the fluid source is empty, an alert may be provided at block 518. For example, a controller of the negative-pressure source 104 can provide an empty bag alert through a user interface of the negative-pressure source 104.

At block 516, if the fluid source is not empty, a negative-pressure source may be turned off and the negative pressure in a cartridge may be vented at block 520. For example, a controller of the negative-pressure source 104 may turn off a pump of the negative-pressure source 104 and vent the negative pressure in the negative-pressure chamber 126 to the ambient environment. At block 522, the negative-pressure source can determine if the total volume of instillation fluid has been provided. For example, a controller of the negative-pressure source 104 can include a counter that increments upwards each time the pump of the negative-pressure source 104 is operated during the instillation therapy cycle. If the therapeutic dose of instillation fluid provided during each operation of the negative-pressure source 104 is known, a controller can determine the total volume of fluid provided through the fluid outlet 120. A controller can then compare the total volume of fluid provided to a predetermined volume of instillation fluid to be provided to determine if the predetermined volume of instillation fluid has been provided. The predetermined volume of instillation fluid required may be based on a total volume prescribed by a clinician. At block 522, if the predetermined volume of instillation fluid has not been provided, the negative-pressure source may be turned on at block 504. At block 522, if the predetermined volume of instillation fluid has been provided, a signal can be provided at block 524 to indicate that the instill sequence is complete. For example, a controller may provide an indication on the user interface of the negative-pressure source 104.

The systems, apparatuses, and methods described herein may provide significant advantages. Example embodiments of the cartridge 112 have been described herein that can be combined with an existing negative-pressure wound treatment therapy system to provide controlled instillation therapy. The cartridge 112 can also be calibrated to provide a dosage of fluid at a pressure suitable for use with a tissue site, for example, approximately 100 mmHg. The cartridge 112 can also be calibrated to provide an accurate dosing of a prescribed amount of fluids. Furthermore, the cartridge can be used with a multi-channel negative-pressure system so that the multi-channel negative-pressure system can provide both instillation and negative-pressure therapy. Alternatively, multiple cartridges can be used with a multi-channel negative-pressure system to provide instillation of multiple different types of fluids. The cartridge 112 may also be combined with a tissue site drain to allow for continuous washing of the tissue site with instillation fluids. Some embodiments may be combined with software suitable for controlling negative-pressure therapy and instillation therapy so that the negative-pressure therapy system may be combined with another negative-pressure therapy system to provide alternating negative-pressure therapy and instillation therapy. Example embodiments may also include a negative-pressure therapy system having the capability to determine if a canister or an instillation cartridge is fluidly coupled to the negative-pressure source and provide an appropriate therapy in response to the determination.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A fluid delivery apparatus for providing instillation therapy with a negative-pressure source, the apparatus comprising:
    a housing having an ambient chamber and a negative-pressure chamber fluidly isolated from each other;
    a moveable barrier disposed in the housing between the ambient chamber and the negative-pressure chamber, the moveable barrier operable to move between a charge position and a discharge position in response to negative pressure;
    a fluid source disposed in the negative-pressure chamber, the fluid source being collapsible in response to movement of the moveable barrier to the discharge position;
    a fluid outlet in fluid communication with the fluid source;
    a negative-pressure port in fluid communication with the negative-pressure chamber and configured to be coupled to a negative-pressure source; and
    a vent formed in the housing and fluidly coupled to the ambient chamber.

2. The apparatus of claim 1, wherein the moveable barrier comprises a diaphragm.

3. The apparatus of claim 1, wherein the moveable barrier comprises a piston.

4. The apparatus of claim 1, further comprising a calibrated orifice disposed in the fluid outlet.

5. The apparatus of claim 1, further comprising an occluder in fluid communication with the fluid outlet.

6. The apparatus of claim 1, further comprising:
    a calibrated orifice disposed in the fluid outlet; and
    an occluder in fluid communication with the fluid outlet.

7. The apparatus of claim 1, further comprising a pressure sensing port fluidly coupled to the negative-pressure chamber.

8. The apparatus of claim 1, further comprising:
    a calibrated orifice disposed in the fluid outlet;
    an occluder in fluid communication with the fluid outlet; and
    a pressure sensing port fluidly coupled to the negative-pressure chamber.

9. A system for providing instillation therapy, the system comprising:
    a negative-pressure source;
    a cartridge coupled to the negative-pressure source, the cartridge comprising:
        a housing having an ambient chamber and a negative-pressure chamber fluidly isolated from each other;
        a moveable barrier disposed in the housing between the ambient chamber and the negative-pressure chamber, the moveable barrier operable to move between a charge position and a discharge position in response to negative pressure;
        a fluid source disposed in the negative-pressure chamber, the fluid source being collapsible in response to movement of the moveable barrier to the discharge position;
        a fluid outlet in fluid communication with the fluid source;
        a negative-pressure port in fluid communication with the negative-pressure chamber and configured to be coupled to the negative-pressure source; and
        a vent formed in the housing and fluidly coupled to the ambient chamber.

10. The system of claim 9, wherein the moveable barrier comprises a diaphragm.

11. The system of claim 9, wherein the moveable barrier comprises a piston.

12. The system of claim 9, further comprising a calibrated orifice disposed in the fluid outlet.

13. The system of claim 9, further comprising an occluder in fluid communication with the fluid outlet.

14. The system of claim 9, further comprising:
    a calibrated orifice disposed in the fluid outlet; and
    an occluder in fluid communication with the fluid outlet.

15. The system of claim 9, further comprising a pressure sensing port fluidly coupled to the negative-pressure chamber.

16. The system of claim 9, further comprising:
    a calibrated orifice disposed in the fluid outlet;
    an occluder in fluid communication with the fluid outlet; and a pressure sensing port fluidly coupled to the negative-pressure chamber.

17. A method for providing instillation therapy with a negative-pressure source, the method comprising:
   providing a negative-pressure source;
   providing a cartridge comprising:
      a housing having an ambient chamber and a negative-pressure chamber fluidly isolated from each other;
      a barrier disposed in the housing between the ambient chamber and the negative-pressure chamber, the barrier operable to move between a charge position and a discharge position in response to negative pressure;
      a fluid source disposed in the negative-pressure chamber, the fluid source being collapsible;
      a fluid outlet in fluid communication with the fluid source;
      a negative-pressure port in fluid communication with the negative-pressure chamber and configured to be coupled to the negative-pressure source; and
      a vent formed in the housing and fluidly coupled to the ambient chamber;
   fluidly coupling the negative-pressure source to the negative-pressure port; and
   supplying negative-pressure to the negative-pressure chamber move the barrier against the fluid source.

18. The method of claim 17, further comprising:
   determining a volume of fluid flowing through the fluid outlet;
   if the volume of fluid equals a therapeutic dosage, stopping the supply of negative pressure; and
   venting the negative-pressure chamber to an ambient environment.

19. The method of claim 17, wherein the cartridge further comprises a calibrated orifice disposed in the fluid outlet, the method further comprising:
   determining a level of negative pressure in the negative pressure chamber;
   calculating a flow rate through the fluid outlet based on the level of negative-pressure in the negative-pressure chamber and a diameter of the calibrated orifice; and
   maintaining the level of negative pressure in the negative-pressure chamber to maintain the flow rate until a therapeutic volume of fluid is provided through the fluid outlet.

20. The method of claim 17, wherein the barrier comprises a diaphragm.

21. The method of claim 17, wherein the barrier comprises a piston.

22. The method of claim 17, further comprising an occluder in fluid communication with the fluid outlet.

23. The method of claim 17, further comprising:
   a calibrated orifice disposed in the fluid outlet; and
   an occluder in fluid communication with the fluid outlet.

24. The method of claim 17, further comprising a pressure sensing port fluidly coupled to the negative-pressure chamber.

25. The method of claim 17, further comprising:
   a calibrated orifice disposed in the fluid outlet;
   an occluder in fluid communication with the fluid outlet; and
   a pressure sensing port fluidly coupled to the negative-pressure chamber.

26. An apparatus for providing negative-pressure therapy and instillation therapy, the apparatus comprising:
   a negative-pressure source;
   a cartridge having an ambient chamber, a negative-pressure chamber, and a fluid source disposed in the negative-pressure chamber; and
   a controller configured to:
      determine a level of negative pressure provided by the negative-pressure source,
      calculate an amount of fluid instilled in response to the level of negative pressure,
      maintain the level of negative pressure if the amount of fluid instilled is less than a therapeutic dose, and
      stop supplying negative pressure with the negative-pressure source if the amount of fluid instilled is equal to or greater than a therapeutic dose.

* * * * *